United States Patent [19]

Parham et al.

[11] Patent Number: 4,596,770

[45] Date of Patent: Jun. 24, 1986

[54] ASSAY OF PEROXIDASE ENZYME ACTIVITY

[75] Inventors: Marc Parham, Sharon, Mass.; William J. Warren, North Smithfield, R.I.

[73] Assignee: Travenol-Genetech Diagnostics, Cambridge, Mass.

[21] Appl. No.: 616,204

[22] Filed: Jun. 1, 1984

[51] Int. Cl.[4] .................... G01N 33/53; C12Q 1/54; C12Q 1/28; C12N 9/96; C12N 9/99
[52] U.S. Cl. .................................... 435/7; 435/14; 435/28; 435/184; 435/188; 435/810
[58] Field of Search ............... 435/7, 14, 28, 188, 435/810, 184, 805

[56] References Cited

U.S. PATENT DOCUMENTS 4,318,984  3/1982  Magers et al. .................... 435/28
4,340,394  7/1982  Magers et al. .................... 435/28

FOREIGN PATENT DOCUMENTS 8001972  11/1981  Netherlands .

OTHER PUBLICATIONS

Bionetics (Litton) Technical Data Catalog No. 8910-04.

*Primary Examiner*—Esther M. Kepplinger

[57] ABSTRACT

The use of aqueous N-methyl pyrrolidone as a solvent for a substrate containing tetraalkyl benzidine chromogen and a peroxide in determining peroxidase enzyme activity provides increased stability of the substrate solution and decreased substrate drift in carrying out enzyme immunoassays or enzyme-linked immunosorbent assays.

10 Claims, No Drawings

ASSAY OF PEROXIDASE ENZYME ACTIVITY

This invention relates to an improved enzyme immunoassay or enzyme-linked immunosorbent assay and pertains more specifically to a solution of tetraalkyl benzidine in aqueous N-methyl pyrrolidone for use together with a peroxide as the chromogen substrate for determining peroxidase enzyme activity, resulting in increased stability of the substrate solution and decreased substrate drift.

Enzyme immunoassay and enzyme-linked immunosorbent assay involve the use of an enzyme such as a peroxidase as a label for the unknown in an assay procedure, and measurement of the enzyme activity as an indication of the amount of the unknown in the sample.

It has previously been proposed in Netherlands published patent application No. 8001972 published Nov. 2, 1981 to employ as the substrate for measuring peroxidase enzyme a 3,3',5,5'-tetraalkyl benzidine chromogen together with a peroxide. As pointed out in the published application, the chromogen cannot effectively be dissolved in water alone and it is proposed to employ in the substrate a solution of the chromogen in a mixture of water with a water-miscible aprotic organic liquid such as dimethyl sulfoxide, 1,4-dioxane, or dimethyl formamide, all of which are toxic or hazardous from a biological standpoint. However, it has been found that such substrate solutions suffer from the disadvantage that the organic liquid, like organic liquids generally, tends to decrease the intensity of color development when the substrate solutions are used for their intended purpose, and that such substrate solutions are unstable at room temperature, exhibiting increased development of color even in the absence of any peroxidase. This change in intensity of background color, termed "substrate drift", greatly limits the utility of such substrate solutions in enzyme immunoassays or enzyme-linked immunosorbent assays.

It has now been found that in an enzyme immunoassay or enzyme-linked immunosorbent assay in which 3,3',5,5'-tetraalkyl benzidine chromogen or an acid salt thereof and a peroxide are reacted with a peroxidase in an aqueous buffered substrate medium, the step of providing the chromogen or acid salt in solution in an aqueous medium containing 5 to 20% by volume of N-methyl pyrrolidone (NMP) provides improved results in the form of increased stability of the substrate solution and decreased substrate drift as well as being free from biohazard and from toxicity.

The chromogens with which the present invention is useful include any 3,3',5,5'-tetraalkyl benzidine in which the alkyl groups each contain from 1 to 5 carbon atoms; particularly useful are 3,3',5,5'-tetramethyl benzidine and 3,3',5,5'-tetraethyl benzidine. Acid salts such as the hydrochloride are also useful. The amount of chromogen present in the substrate solution may vary over a considerable range, depending upon the identity and concentration of the peroxidase enzyme whose activity is to be measured; in general, the concentration of chromogen may vary from 0.5 to 10 mM, preferably from 1 to 3 mM. The amount of peroxide present may also vary, depending upon the amount of chromogen present, ranging from 1 to 20 mM, but preferably is from 1 to 6 mM. Any of the usual peroxides such as hydrogen peroxide, urea peroxide, or the like can be employed in the substrate solution. It is also desirable to include a buffer in the solution such as an acetate buffer which maintains the pH at 4 to 7.

The amount of N-methyl pyrrolidone present in the aqueous substrate mixture depends upon the concentration of the chromogen present; higher concentrations of chromogen require higher concentrations of NMP to solubilize the chromogen. In general, it is desired to minimize the concentration of NMP. It is found that the amount of NMP required to solubilize the chromogen is much less than the amount of 1,4-dioxane or of dimethyl sulfoxide required to solubilize the chromogen to the same extent. While concentrations of NMP from 5 to 20% by volume of the water may be used, it is preferred to use from 5 to 10% by volume. Excellent results are obtained using from 6 to 8% by volume when the concentration of the chromogen is of the order of 1–2 mM.

The substrate solution of the present invention is preferably freshly prepared before use by mixing a first stock solution comprising an aqueous solution containing 5–50% N-methyl pyrrolidone by volume and 1–10 mM 3,3',5,5'-tetraalkyl benzidine or an acid salt thereof with a second stock solution comprising an aqueous buffer solution containing 4–40 mM peroxide, and with water if necessary to achieve the desired concentration. The stock solutions can be supplied in the form of a kit which contains in addition a supply of conventional stopping agent solution, antibody- or antigen-coated containers, and antigen standards.

The improvement of the present invention can be used to determine peroxidase activity of any enzyme which catalyzes the reaction of the chromogen with peroxide to form a colored compound. Although peroxidases such as horseradish peroxidase are among the more widely used of such enzymes, there may also be used other peroxidases.

The determination of enzyme activity is carried out in the usual manner by incubating the substrate solution with the specimen containing the enzyme to develop a visible color. For quantitative determinations the reaction with the substrate solution is stopped after an established time by adding a conventional stopping agent such as, for example, an aqueous solution of a water-soluble fluoride, such as sodium fluoride, at pH 3–6; or acids such as sulfuric acid, hydrochloric acid, etc. A soluble fluoride is preferred because it provides a stable blue color.

The improvement of the present invention can be employed with any of the usual enzyme immunoassay procedures, either homogeneous or heterogeneous assays, and either single- or double-antibody assays, and including enzyme-linked immunosorbent assays.

A concentration of 1.5 mM 3,3',5,5'-tetramethyl benzidine was found to be satisfactory for measuring the peroxidase enzyme activity of horseradish peroxidase. Approximately 7.5% by volume of N-methyl pyrrolidone in water was found capable of maintaining in solution at room temperature an amount of chromogen equal to 1.5 mM. Approximately the same amount of dimethyl formamide was found to be equally effective in maintaining such a concentration of chromogen in solution, but approximately 15% by volume of dimethyl sulfoxide or of 1,4-dioxane was required to maintain clarity of such a 1.5 mM solution. A visible yellow coloration appeared when the chromogen was mixed with water and dioxane, the intensity of the color being proportional to the amount of dioxane present. Consequently, the mixture of water with dioxane could not be employed in determining enzyme activity because of excessive background color.

The following examples are intended to illustrate more fully the nature of the present invention without acting as a limitation upon its scope.

EXAMPLE 1

Three aqueous substrate solutions were prepared, as follows:
A. Water containing 15% by volume dimethyl sulfoxide
B. Water containing 7.5% by volume dimethyl formamide
C. Water containing 7.5% by volume N-methyl pyrrolidone.

Each solution contained in addition 1.5 mM 3,3',5,5'-tetramethyl benzidine, 4 mM hydrogen peroxide, and 80 mM sodium acetate.

Each substrate solution was allowed to stand at room temperature, and its absorption at 370 nm was measured in a spectrophotometer, using water as a blank standard, at intervals following preparation with the following results:

| Time After Preparation, Hours | Absorption at 370 nm. | | |
|---|---|---|---|
| | Solution A | Solution B | Solution C |
| 0 | .029 | .02 | .014 |
| 0.5 | .125 | .062 | .033 |
| 1.5 | .205 | .104 | .051 |
| 2.0 | .295 | .142 | .07 |
| 2.5 | .364 | .181 | .086 |
| 3.0 | .435 | .216 | .108 |
| 3.5 | .504 | .249 | .13 |
| 4.0 | .566 | .278 | .152 |
| 5.0 | .621 | .302 | .171 |

As can be seen, the solution containing N-methyl pyrrolidone displayed substantially less initial absorption than did the other two solutions; in addition, absorption by this solution increased at a much lower rate than did that of the other two solutions, evidence of substantially decreased substrate drift. Consequently, the time during which freshly prepared substrate solutions containing N-methyl pyrrolidone can be used to measure activity of the peroxidase before background levels of color absorption become unacceptable is significantly extended as compared to the other aprotic organic solvents.

In addition, it was found that the use of conventional stopping agents such as acid, or sodium fluoride in acetate buffer at pH 3-6 provided stability of the color intensity for more than 30 minutes in the case of substrate solutions containing N-methyl pyrrolidone when used to measure activity of horseradish peroxidase.

EXAMPLE 2

A standard test solution was prepared in the form of a conjugate of horseradish peroxidase with anti-human IgG diluted 1:1000 in an aqueous buffer of TRIS (50 mM), bovine serum albumin (1%) polyoxyethylene sorbitan monolaurate (polysorbate 20) (0.05%), and sodium azide (0.1%), pH 7.8 (all percentages by weight). An aqueous substrate solution was prepared containing 3,3',5,5'-tetramethyl benzidine (1.5 mM), N-methyl pyrrolidone (7.5% by volume), hydrogen peroxide (4 mM), and sodium acetate (80 mM), pH 5.1.

A series of tests was carried out by mixing each of several 20 μL aliquots of the standard test solution with 200 μL of the substrate solution and allowing each mixture to incubate at room temperature for varying periods of time to generate a color signal. Each was then stopped by adding to it with mixing 0.5 mL of an aqueous stop solution containing sodium fluoride (0.1% by weight) and sodium acetate (20 mM), adjusted to pH 3.5 with hydrochloric acid. Each specimen was measured by determining absorption in a spectrophotometer at 370 nm, using the stopped substrate solution as a blank standard, once immediately after stopping, and again thirty minutes later. The results were as shown in the following table:

| Time Period of Signal Generation, min. | Absorption | |
|---|---|---|
| | Immediately after Stopping | Thirty Minutes After Stopping |
| 10 | 0.118 | 0.114 |
| 15 | 0.178 | 0.172 |
| 20 | 0.230 | 0.223 |
| 25 | 0.287 | 0.280 |
| 30 | 0.346 | 0.340 |

A stopped substrate solution containing no horseradish peroxidase conjugate measured 0.017 immediately after stopping and 0.018 thirty minutes later as compared to a water blank.

The same test procedure carried out with a substrate solution containing 15% dimethyl sulfoxide instead of N-methyl pyrrolidone produced very similar results except that the measurements of the substrate blank solution were approximately twice as high.

EXAMPLE 3

A prototype enzyme immunoassay kit was developed containing the following solutions as the enzyme substrate components:
1. 3,3',5,5'-tetramethyl benzidine (7.5 mM), N-methyl pyrrolidone (40% by volume).
2. Hydrogen peroxide (5 mM), sodium acetate (100 mM), pH 5.0.
3. Sodium fluoride (0.2% by weight), sodium acetate (20 mM), pH 3.5.
4. Frozen (−4° C.) 1:1000 dilution of horseradish peroxidase conjugated with antihuman IgG in aqueous buffer containing TRIS (50 mM), bovine serum albumin (1%), polyoxyethylene sorbitan monolaurate (polysorbate 20) (0.05%), and sodium azide (0.01%), pH 7.8 (all percentages by weight).

Solutions 1-3 were stored at room temperature, solution 4 at −4° C. At intervals during storage aliquots of solution (1) were diluted with solution (2) at a ratio of 1 to 4 to provide a working substrate solution containing 1.5 mM 3,3',5,5'-tetramethylbenzidine and 4 mM hydrogen peroxide. Aliquots of solution (4) were thawed daily. The solutions were then tested by the procedure described in Example 2 above except that only 5 minutes was allowed for signal generation and 10 readings for each test were made and averaged immediately after stopping signal generation. The results were highly consistent, varying between 1.029 and 1.102 for periods of storage up to 50 days. This period of stable storage of stock solutions is adequate for practical utility.

What is claimed is:
1. In an enzyme immunoassay or enzyme-linked immunosorbent assay in which 3,3',5,5'-tetraalkyl benzidine chromogen or an acid salt thereof and a peroxide are reacted with a peroxidase in an aqueous buffer, said reaction is stopped by the addition of a stopping agent, and the intensity of the color developed is measured, the improvement which comprises providing said chromogen in solution in an aqueous substrate medium containing 5 to 20% by volume of N-methyl pyrrolidone and an acetate buffer providing a pH from 4 to 7.

2. An assay as claimed in claim 1 in which the concentration of said chromogen is from 1 to 2 mM and the concentration of N-methyl pyrrolidone is 6 to 8% by volume.

3. An assay as claimed in claim 1 in which said chromogen is 3,3′,5,5′-tetramethyl benzidine or an acid salt thereof.

4. An assay as claimed in claim 2 in which said chromogen is 3,3′,5,5′-tetramethyl benzidine or an acid salt thereof and the concentration of N-methyl pyrrolidone is 6 to 8% by volume.

5. An assay as claimed in claim 1 in which said reaction is stopped by the addition of an aqueous solution of water soluble fluoride at pH 3–6.

6. An assay as claimed in claim 2 in which said reaction is stopped by the addition of an aqueous solution of water soluble fluoride at pH 3–6.

7. An assay as claimed in claim 3 in which said reaction is stopped by the addition of an aqueous solution of water soluble fluoride at pH 3–6.

8. An assay as claimed in claim 4 in which said reaction is stopped by the addition of an aqueous solution of water soluble fluoride at pH3–6.

9. A stock solution for use in an enzyme immunoassay or enzyme-linked immunosorbent assay procedure comprising reacting 3,3′,5,5′-tetraalkylbenzidine chromogen and peroxide with peroxidase in an aqueous substrate medium, said solution comprising an aqueous solution containing 5–50% N-methyl pyrrolidone by volume, 1–10 mM 3,3′,5,5′-tetraalkyl benzidine or an acid salt thereof, and an acetate buffer providing a pH from 4 to 7.

10. A stock solution for use in an enzyme immunoassay or enzyme-linked immunosorbent assay procedure comprising reacting 3,3′,5,5′-tetraalkylbenzidine chromogen and peroxide with peroxidase, said solution consisting essentially of an aqueous solution containing 5–50% N-methyl pyrrolidone by volume and 1–10 mM 3,3′,5,5′-tetraalkyl benzidine or an acid salt thereof.

* * * * *

UNITED STATES PATENT AND TRADEMARK OFFICE
CERTIFICATE OF CORRECTION

PATENT NO. : 4,596,770
DATED : June 24, 1986
INVENTOR(S) : Marc Parham et al.

It is certified that error appears in the above-identified patent and that said Letters Patent are hereby corrected as shown below:

Name of Assignee should be "Travenol-Genentech Diagnostics"

Signed and Sealed this

Sixteenth Day of September 1986

[SEAL]

Attest:

DONALD J. QUIGG

Attesting Officer  Commissioner of Patents and Trademarks